United States Patent [19]
Farzin-Nia et al.

[11] Patent Number: 5,692,895
[45] Date of Patent: Dec. 2, 1997

[54] LUMINESCENT ORTHODONTIC APPLIANCES

[75] Inventors: Farrokh Farzin-Nia, Inglewood; Ronald M. Malerstein, Huntington Beach; Albert Ruiz-Vela, Alto Loma, all of Calif.

[73] Assignee: Ormco Corporation, Glendora, Calif.

[21] Appl. No.: 380,500

[22] Filed: Jan. 30, 1995

[51] Int. Cl.$^6$ ........................................... A61C 3/00
[52] U.S. Cl. ................................. 433/8; 433/18; 433/20
[58] Field of Search ............................... 433/6, 8, 15, 17

[56] References Cited

U.S. PATENT DOCUMENTS

| | | | |
|---|---|---|---|
| 4,433,959 | 2/1984 | Faunce | 433/222.1 |
| 4,784,606 | 11/1988 | Jones et al. | 433/8 |
| 5,007,924 | 4/1991 | Jekel | 606/234 |
| 5,011,403 | 4/1991 | Sadoun et al. | 433/8 |
| 5,074,783 | 12/1991 | Reher | 433/8 |
| 5,083,919 | 1/1992 | Quach | 433/6 |
| 5,145,365 | 9/1992 | Farzin-Nia | 433/8 |
| 5,211,748 | 5/1993 | Robinson et al. | 106/35 |
| 5,231,062 | 7/1993 | Mathers et al. | 433/8 |
| 5,318,440 | 6/1994 | Adam et al. | 433/8 |

OTHER PUBLICATIONS

Brochure, "Color! Personalize, Customize", Allesee Orthodontic Applicances, Inc., P.O. Box 725, Sturtevant, WI 53177.

Primary Examiner—Nicholas D. Lucchesi
Attorney, Agent, or Firm—Wood, Herron & Evans L.L.P.

[57] ABSTRACT

Luminescent orthodontic appliances, such as brackets, archwires, bands and the like, having a luminescent pigment or mixture of luminescent pigments are described. In a preferred form, the luminescent pigment is a phosphorescent pigment comprising zinc sulfide doped with copper. The pigment gives the appliance a natural appearance in daylight and causes it to emit a greenish-white light in the dark after having been energized by an excitation light source. If desired, the luminescent orthodontic appliance may be made with a fluorescent pigment or a combination of fluorescent and phosphorescent pigments. If a fluorescent pigment is used, the bracket will exhibit a luminescence in daylight; whereas if a mixture of fluorescent and phosphorescent pigments are used, the appliance will luminesce in the dark after having been exposed to a light source, in addition to exhibiting a luminescence in the daylight. The luminescent appliances of this invention provide a fun alternative to traditional orthodontic appliances, particularly for younger patients, who can "show off" their braces to their families and friends.

30 Claims, No Drawings

LUMINESCENT ORTHODONTIC APPLIANCES

FIELD OF THE INVENTION

This invention relates to orthodontic appliances, and more particularly to orthodontic appliances which are luminescent.

BACKGROUND OF THE INVENTION

Over the years, orthodontic appliances, such as brackets, archwires, bands, and the like, have evolved to meet various orthodontic and aesthetic demands of both orthodontists and patients. For example, generally clear or tooth-enamel colored plastic brackets have been developed, in part, to appeal to patients who want their orthodontic work to blend in with the natural appearance of their teeth.

However, it is believed that there is another segment of the orthodontic patient population, particularly younger patients, that would enjoy an orthodontic system which not only straightens the teeth but also is fun to wear and provides a unique, even colorful appearance. Therefore, what is needed are orthodontic components, for example, an orthodontic bracket or archwire, which are not only effective in providing orthodontic treatment, but also are fun for patients, especially younger patients, to wear.

SUMMARY OF THE INVENTION

In its broadest aspects, the invention is directed to luminescent orthodontic appliances. As used herein, "orthodontic appliance" refers to any orthodontic component fixed in the mouth for a period of time to assist in the correction of the bite and tooth position. Examples of orthodontic appliances include, but are not limited to, brackets, archwires and bands. The luminescent appliances of the present invention bring an element of "fun" into orthodontic treatment, by allowing patients, especially younger patients, to show off their "glow in the dark" braces to their friends and families. Furthermore, such appliances offer several benefits, such as increased patient appeal and satisfaction because of the fun colors and glow effect, while simultaneously providing an effective orthodontic treatment.

In one embodiment of the invention, orthodontic brackets are made of an orthodontic bracket material including a luminescent pigment. Typically, the bracket material is plastic, ceramic or metal. If plastic is used, preferably the plastic comprises polycarbonate, and more preferably, the polycarbonate is reinforced with glass fibers. In a preferred form of the invention, the glass fibers comprise in the range of about 20% to about 40% by weight of the bracket material.

Suitable luminescent pigments may be phosphorescent pigments, or fluorescent pigments, or mixtures thereof. Examples of phosphorescent pigments are zinc sulfide doped with copper, zinc sulfide doped with copper and manganese, and mixtures thereof. Preferably, the luminescent pigment comprises in the range of about 10% to about 15% by weight of the bracket material. The luminescent pigment may be dispersed within the bracket material or deposited onto the exposed bracket surfaces. If the pigment is deposited, methods such as glazing, bombarding, ion-beam implantation, plasma coating and the like may be used. In a preferred embodiment, the luminescent pigment is a phosphorescent pigment comprising zinc sulfide doped with copper. This pigment has the advantage of giving the bracket a generally natural appearance in the daylight, while enabling the bracket to emit a greenish white after-glow in the dark or dim lighting conditions after the bracket has been subjected to a light source. If desired, other luminescent pigments may be used to create different daylight and after-glow colors.

In an alternative embodiment, the invention is directed to orthodontic archwires which include a luminescent pigment. Typically, the pigment is a phosphorescent and/or fluorescent pigment which is coated onto the archwire using a method such as glazing, bombarding, ion-beam implantation, plasma coating and the like.

These and other features and advantages of the present invention will become apparent to persons skilled in the art upon review of the following more detailed description.

DETAILED DESCRIPTION OF THE INVENTION

In the luminescent orthodontic bracket embodiment of the invention, the bracket comprises an orthodontic bracket material including a luminescent pigment. Typically, the bracket material is plastic, ceramic or metal, and if plastic is used, the plastic may be any of a number of plastics used in orthodontic brackets, as are well known in the art. Preferably, the plastic is polycarbonate. In order to improve the rigidity and strength of the bracket, it is preferred to reinforce the plastic with glass fibers. Reinforcing glass fibers preferably are present in the plastic in the range of about 20% to about 40% by weight of the bracket material. This range provides a more desired balance of strength and physical appearance. Below about 20%, the mechanical strength in the wings of the bracket body portion may be reduced, subjecting the brackets to premature failure. Above about 40%, the increased opacity of the brackets due to the glass makes the brackets less pleasing aesthetically and therefore less desirable to some patients.

The bracket material further includes a luminescent pigment. Any one of a number of luminescent pigments may be used to advantage. Examples include pigments with a generally natural or tooth colored appearance when seen in the daylight, pigments with a distinct daylight body color, and pigments which emit a particular color of light in the dark for several minutes or hours after having been exposed to a light source. One of the preferred pigments for use in the present invention is a pigment consisting of crystals of zinc sulfide doped with copper. This particular pigment allows the plastic bracket to maintain a relatively natural tone in the daylight, while providing the classic "glow in the dark" appearance after having been subjected to a light source. The glow itself is due to the unique properties of crystalline zinc sulfide, while copper is added as an activator. The copper allows the crystals to absorb light and slowly emit that light over time.

If desired, the body portion of the bracket may include a mixture of both phosphorescent pigment and fluorescent pigment. The fluorescent pigment gives the bracket a luminescence in normal daylight, while the phosphorescent pigment gives the bracket the "glow in the dark" luminescence. Furthermore, if only a daylight luminescence is desired, the plastic orthodontic bracket may be made incorporating only fluorescent pigment, as opposed to a combination of both fluorescent and phosphorescent pigments. Such phosphorescent pigments, fluorescent pigments and mixtures thereof are available from vendors such as United Mineral & Chemical Corp. (UMC), 1100 Valley Brook Avenue, Lyndhurst, N.J. 07071 under the following designations: GSSU, GSS, GFP and GSR.

Depending upon the particular pigment selected, the bracket may have a natural daylight appearance or a colorful daylight appearance. Several daylight colors are available, including for example, yellow, orange, red, green and blue. In addition, several phosphorescent pigments are available, each emitting a different color after-glow in the dark. As discussed above, the traditional "glow in the dark" phosphorescent pigment comprises crystals of zinc sulfide doped with copper. This pigment appears natural in the daylight and emits a greenish-white light in the dark after being activated by a light source. In addition, other phosphorescent pigments are available which emit other colors in the dark, such as for example yellow, orange or blue. The yellow and orange emitting pigments comprise zinc sulfide doped with copper and manganese, while the blue emitting pigment comprises calcium and strontium sulfide doped with bismuth.

The brackets of this invention may be made by conventional molding techniques as are well known in the art, and preferably, the brackets are made by injection molding techniques. In addition, the pigment is added to the plastic composition using standard pigmentation methods. Examples of such methods include dispersing the pigment within the bracket material or depositing the pigment onto the exposed surfaces of the bracket material. With pigment deposition, methods such as glazing, bombarding, ion-beam implantation, plasma coating and the like may be used. In a preferred form of the invention, the pigment comprises in the range of about 10% to about 15% by weight of the bracket material. It has been found that this range provides a desired level of luminescence while also maintaining the translucent nature of the bracket.

Other luminescent orthodontic appliances as contemplated by the invention may employ the same phosphorescent and/or fluorescent pigments to similar advantage. With respect to the invention, "orthodontic appliance" means any orthodontic component fixed in the mouth for a period of time to assist in the correction of the bite and tooth position. Examples include, but are not limited to, brackets, archwires and bands. Because different orthodontic appliances are made of different types of materials, pigmentation of the various types of appliances may be accomplished by suitable pigmentation techniques. Such techniques include dispersal of the pigment within the appliance material or pigment deposition onto the exposed surfaces of the appliance. Suitable deposition techniques such as glazing, bombarding, ion-beam implantation, plasma coating and the like may be used.

The luminescent orthodontic appliances of the invention are activated to glow in the dark by exposing them to a light source. The intensity and duration of the after-glow depends on several factors including pigment particle size, pigment concentration, type of excitation light source and intensity of light source. Depending upon the balance of these factors, the glow may be perceptible for a period ranging from a few minutes to several hours. The preferred excitation light source for use with the present invention is a standard tungsten filament incandescent light source. Although ultraviolet light is a more potent excitation light source, it is not recommended for use in energizing the bracket because, in sufficient quantities, it may be harmful to the eyes and skin.

It is to be understood that the invention is not to be construed as limited to the preferred embodiments and examples recited herein, and that various changes and modifications may be made to the invention without departing from the scope thereof, which is defined by the following claims.

What is claimed is:

1. A luminescent orthodontic bracket, comprising:
   an orthodontic bracket material including a nonremovable luminescent pigment.

2. The bracket of claim 1 wherein said bracket material is selected from the group consisting of plastic, ceramic and metal.

3. The bracket of claim 1 wherein said bracket material is plastic.

4. The bracket of claim 3 wherein said plastic is polycarbonate.

5. The bracket of claim 4 wherein said polycarbonate further includes reinforcing glass fibers.

6. The bracket of claim 5 wherein said glass fibers comprise in the range of about 20% to about 40% by weight of said bracket material.

7. The bracket of claim 1 wherein said luminescent pigment comprises in the range of about 10% to about 15% by weight of said bracket material.

8. The bracket of claim 1 wherein said luminescent pigment is selected from the group consisting of a phosphorescent pigment, a fluorescent pigment, and mixtures thereof.

9. The bracket of claim 8 wherein said phosphorescent pigment is selected from the group consisting of zinc sulfide doped with copper, zinc sulfide doped with copper and manganese, and mixtures thereof.

10. The bracket of claim 1 wherein said luminescent pigment is dispersed within said bracket material.

11. The bracket of claim 1 wherein said luminescent pigment is deposited onto said bracket material.

12. The bracket of claim 11 wherein said pigment is glazed, bombarded, ion-beam implanted or plasma coated.

13. The bracket of claim 1 wherein said luminescent pigment includes a phosphorescent pigment.

14. The bracket of claim 13 wherein said bracket material includes plastic.

15. The bracket of claim 14 wherein said luminescent pigment is dispersed within said bracket material.

16. The bracket of claim 1 wherein said luminescent pigment is a phosphorescent pigment.

17. A phosphorescent plastic orthodontic bracket, comprising:
   a plastic bracket material including a phosphorescent pigment dispersed therein;
   said plastic bracket material being polycarbonate reinforced with glass fibers, said fibers comprising in the range of about 20% to about 40% by weight of said plastic bracket material;
   said phosphorescent pigment comprising zinc sulfide doped with copper, said pigment comprising in the range of about 10% to about 15% by weight of said plastic bracket material.

18. A luminescent orthodontic archwire, comprising:
   an orthodontic archwire including a nonremovable luminescent pigment.

19. The archwire of claim 18 wherein said pigment is coated onto said archwire.

20. The archwire of claim 19 wherein said pigment is glazed, bombarded, ion-beam implanted or plasma coated.

21. The archwire of claim 18 wherein said luminescent pigment is selected from the group consisting of a phosphorescent pigment, a fluorescent pigment, and mixtures thereof.

22. The archwire of claim 18 wherein said pigment comprises a phosphorescent pigment.

23. The archwire of claim 22 wherein said phosphorescent pigment is selected from the group consisting of zinc sulfide doped with copper, zinc sulfide doped with copper and manganese, and mixtures thereof.

24. The archwire of claim 23 wherein said phosphorescent pigment is coated onto said archwire.

25. A luminescent orthodontic appliance used to move teeth in the correction of bite and tooth position, comprising:

an orthodontic appliance which moves or assists in moving of teeth in the correction of bite and tooth position, said orthodontic appliance comprising:

an orthodontic appliance material including a nonremovable luminescent pigment.

26. The appliance of claim 25 wherein said orthodontic appliance material is selected from the group consisting of plastic, ceramic and metal.

27. The appliance of claim 25 wherein said pigment is selected from the group consisting of a phosphorescent pigment, a fluorescent pigment, and mixtures thereof.

28. The appliance of claim 25 wherein said pigment is dispersed within said orthodontic appliance material.

29. The appliance of claim 25 wherein said pigment is deposited onto said orthodontic appliance material.

30. The appliance of claim 29 wherein said pigment is glazed, bombarded, ion-beam implanted or plasma coated.

* * * * *